(12) United States Patent
Park et al.

(10) Patent No.: US 6,606,394 B1
(45) Date of Patent: Aug. 12, 2003

(54) SURFACE INSPECTING APPARATUS AND METHOD THEREFOR

(75) Inventors: Chang Joon Park, Taejon (KR); Hyeon Jin Kim, Taejon (KR); Weon Geun Oh, Taejon (KR)

(73) Assignee: Electronics and Telecommunications Research Institute, Taejon (KR)

( * ) Notice: Subject to any disclaimer, the term of this patent is extended or adjusted under 35 U.S.C. 154(b) by 0 days.

(21) Appl. No.: 09/475,119

(22) Filed: Dec. 30, 1999

(30) Foreign Application Priority Data

Dec. 9, 1999 (KR) .............................................. 99-56196

(51) Int. Cl.[7] ................................................. G06K 9/00
(52) U.S. Cl. ...................................................... 382/108
(58) Field of Search ................................. 382/141, 143, 382/144, 108, 145

(56) References Cited

U.S. PATENT DOCUMENTS 4,817,184 A  *  3/1989  Thomason et al.  .........  382/141

FOREIGN PATENT DOCUMENTS

| JP | 11-66311 | 3/1999 | ............. G06T/7/00 |
| KR | 94-5944 | 3/1994 | ............. G01B/11/30 |
| KR | 95-12538 | 5/1995 | ............. H01J/9/42 |
| KR | 96-11383 | 4/1996 | ............. G01B/11/24 |

* cited by examiner

Primary Examiner—Leo Boudreau
Assistant Examiner—Tom Y. Lu
(74) Attorney, Agent, or Firm—Jacobson Holman PLLC

(57) ABSTRACT

A surface inspecting apparatus comprises an image achieving unit for achieving an image of a surface of an object; and a controller for providing the symmetry feature of the spot or contaminant by using the magnitude of the intensity gradient and the orientation of the intensity gradient for each pixel of the achieved surface image to thereby detect a spot or contaminant on the surface. The controller detects the spot or contaminant by using a symmetry magnitude map formed by the magnitude of the intensity gradient and the orientation of the intensity gradient of each pixel, after achieving the magnitude of the intensity gradient and the orientation of the intensity gradient by using a gradient operator on the achieved surface image, wherein the symmetry magnitude map provides the internal symmetry feature of the spot or contaminant.

9 Claims, 4 Drawing Sheets

SURFACE INSPECTING APPARATUS AND METHOD THEREFOR

BACKGROUND OF THE INVENTION

1. Field of the Invention

The present invention relates to a visual inspection technology using image processing, and more particularly, to a surface inspecting apparatus for detecting a spot or contaminant on a surface of an object, regardless of the intensity gradient on the surface and pattern presence on the surface, by taking the surface image of the object to use internal symmetry feature of the spot or contaminant and a method therefor. The present invention further relates to a computer-readable recording medium for storing a program for implementing the above method.

2. Description of the Prior Art

Conventionally, in order to detect a spot on a surface of an object, there are several methods, such as a spot detecting method using a binary quantization scheme for an input image and another spot detecting method using, sequentially, smoothing space filtering scheme where a value of a reference pixel is given by an average of the intensity value of the reference pixel and intensity values of adjacent pixels around the reference pixel and space filtering scheme exhibiting the difference between the intensity value of the reference pixel and the intensity values of the adjacent pixels around the reference pixel.

However, since the conventional spot detecting methods as described above detect the spots based on the difference between the intensity value of the reference pixel and the intensity values of the adjacent pixels around the reference pixels, they are applicable to the surface which has uniform intensity thereon and has no pattern in the background thereof. That is, the conventional methods can not be applied when the intensity of the surface to be inspected is non-uniform or there is pattern on the surface to be inspected.

SUMMARY OF THE INVENTION

It is, therefore, a primary object of the invention to provide a surface inspecting apparatus for detecting a spot or contaminant even if the surface has non-uniform intensity thereon or it has pattern thereon, a method therefor and a computer-readable recording medium for storing a program for implementing the method.

That is, the object of the present invention is to provide a surface inspecting apparatus capable of, differing from detecting spots based on the difference between intensity value of a reference pixel and the intensity values of the adjacent pixels around the reference pixels, detecting a spot or contaminant when the intensity of the surface to be inspected is non-uniform or there is pattern on the surface to be inspected by exhibiting the internal symmetry feature of the spot or contaminant by using the magnitude of the intensity gradient and the orientation of the intensity gradient of input pixels of a surface image, a method therefor and a computer-readable recording medium for storing the program for realizing the method.

In accordance with one aspect of the present invention, there is provided a surface inspecting apparatus comprising an image achieving unit for achieving an image of a surface of an object; and a controller for providing the symmetry feature of the spot or contaminant by using the magnitude of the intensity gradient and the orientation of the intensity gradient for each pixel of the achieved surface image to thereby detect a spot or contaminant on the surface, wherein the controller detects the spot or contaminant by using a symmetry magnitude map formed by the magnitude of the intensity gradient and the orientation of the intensity gradient of each pixel, after achieving the magnitude of the intensity gradient and the orientation of the intensity gradient by using a gradient operator on the achieved surface image, wherein the symmetry magnitude map provides the internal symmetry feature of the spot or contaminant.

In accordance with another aspect of the present invention, there is provided a method for inspecting a surface of an object, for use in a surface inspecting apparatus, comprising the steps of: first achieving the magnitude of the intensity gradient and the orientation of the intensity gradient of each pixel in the image of the surface by using a gradient operator; second achieving a symmetry magnitude map by using the magnitude of the intensity gradient and the orientation of the intensity gradient of each pixel, wherein the symmetry magnitude map exhibits the internal symmetry feature of a spot or contaminant on the surface; and detecting the spot or contaminant by using the symmetry magnitude map.

In accordance with still another aspect of the present invention, there is provided a computer-readable recording medium for storing a program, the program implementing in an apparatus having a large capability processor for inspecting a surface of an object, first function for achieving the magnitude of the intensity gradient and the orientation of the intensity gradient for each pixel of the image of the surface by using a gradient operator on the image; second function for achieving symmetry magnitude map exhibiting symmetry feature of a spot or contaminant by using the magnitude of the intensity gradient and the orientation of the intensity gradient; and third function for detecting the spot or contaminant by using the symmetry magnitude map.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PREFERRED EMBODIMENTS

Hereinafter, it will be described in detail for a preferred embodiment of the invention with reference to the accompanying drawings.

Figure 1:
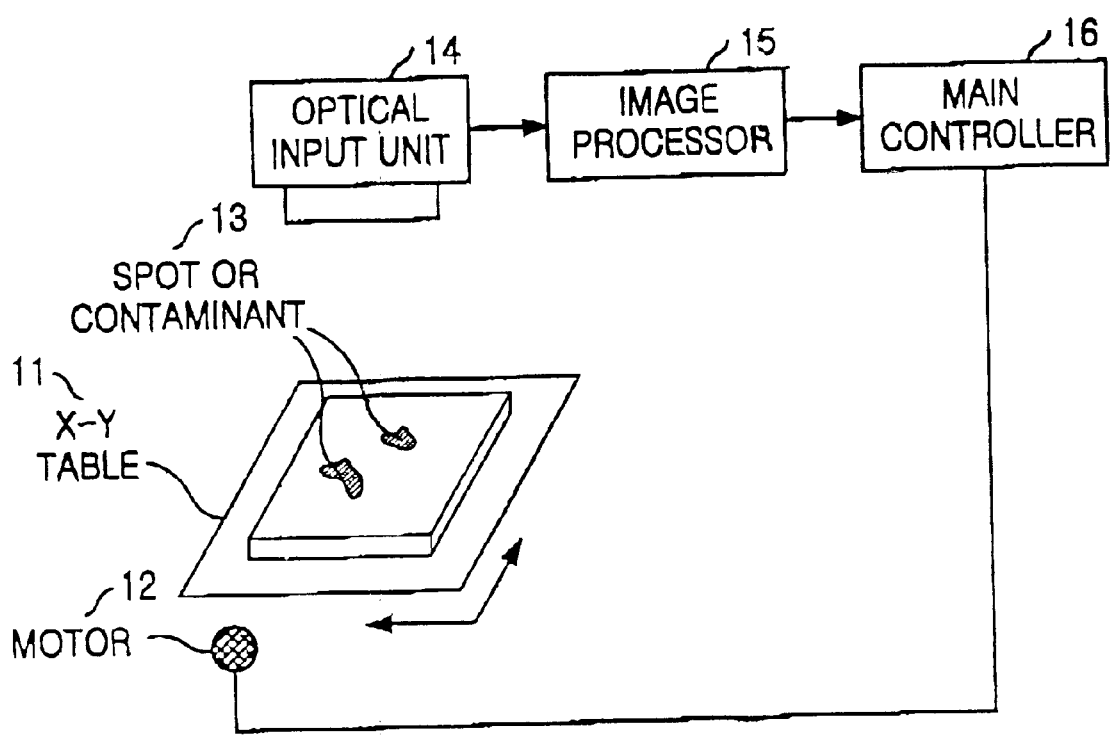
FIG. 1 represents an embodiment of a surface inspecting apparatus in accordance with the present invention.

FIG. 1 shows a structure diagram of an embodiment of a surface inspecting apparatus of the present invention.

The inventive apparatus comprises a main controller 16, a motor 12 for providing driving power, which is driven under the control of the main controller 16, an X-Y table 11 using the driving power from the motor 12 for moving position of an object to be inspected, an optical input unit 14 for achieving 2 dimensional image of the surface of the object placed on the X-Y table 11, and an image processor 15 for processing the image input applied thereto through the optical input unit 14 and for transferring the processed image to the main controller 16. The main controller 16 detects the spot or contaminant on the surface of the object by achieving a symmetry magnitude map.

The symmetry magnitude map exhibits the internal symmetry feature of the spot or contaminant and is formulated by using two kind of information, the magnitude of the intensity gradient and the orientation of the intensity gradient for each pixel of the surface image. The two kind of information are achieved by using gradient operator on the surface image of the object.

Herein, the X-Y table 11 is moved to input the whole surface image with required resolution if the whole surface image of the object can not be inputted as a single image. That is, the X-Y table 11 makes it possible to input the whole surface image of high resolution by inputting the several images into which the whole image is divided by moving the object in a first direction or in a second direction.

Next, the detailed operation of the above surface inspecting apparatus will be described with reference to FIG. 2.

Figure 2:
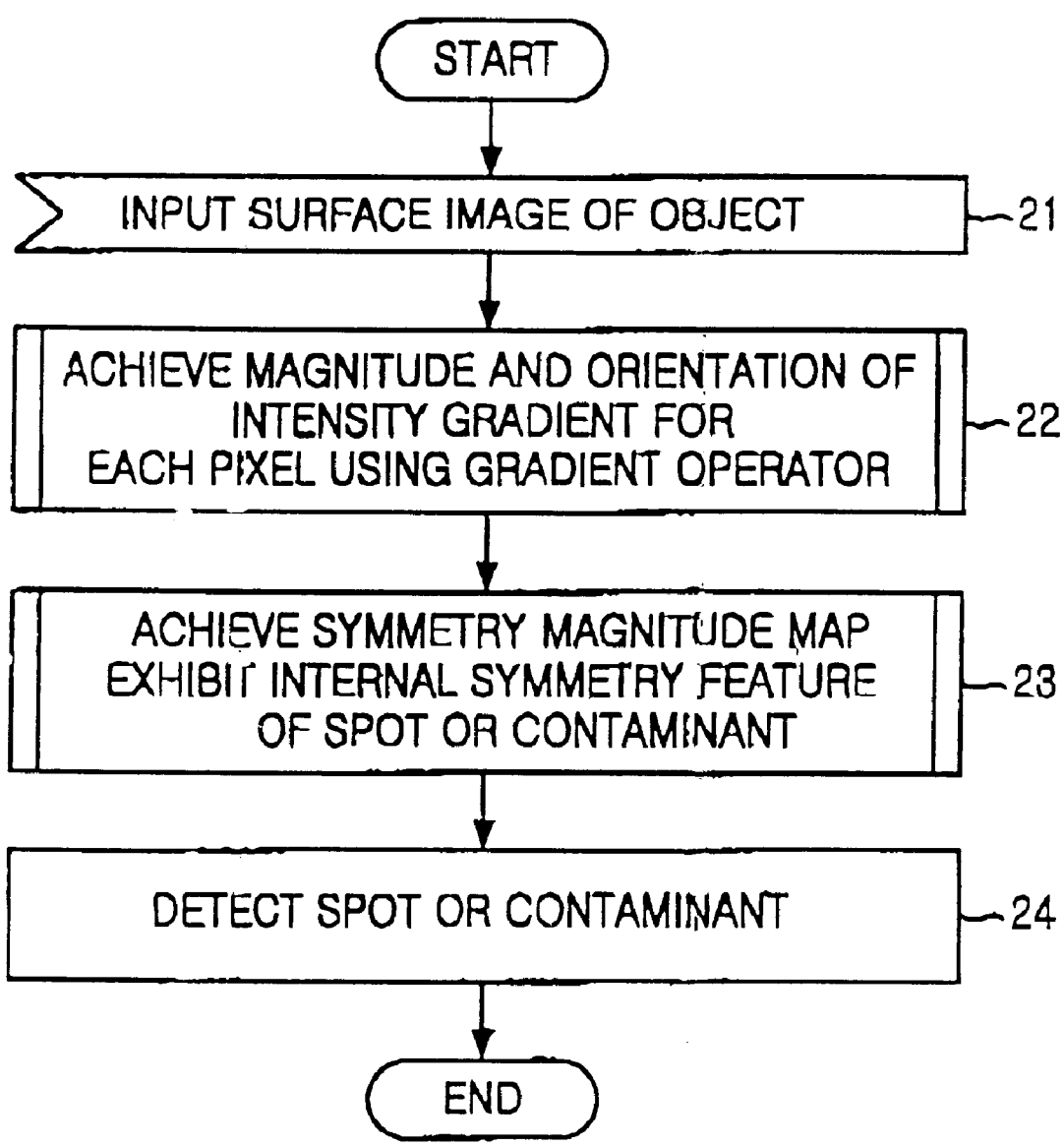
FIG. 2 shows an overall flow chart for the embodiment of the surface inspecting apparatus in accordance with the present invention.

FIG. 2 is an overall flow chart of an embodiment of an inventive surface inspecting method.

First, through the X-Y table 11, the optical input unit 14 and the image processor 15, the surface image of the object is inputted at step 21 to extract the two kind of information, the magnitude of the intensity gradient and the orientation of the intensity gradient for each pixel, by using the gradient operator at step 22.

And then, the symmetry magnitude map exhibiting the internal symmetry feature of the spot or contaminant is formulated by using the two kind of information at step 23.

At that time, since the spot or contaminant, typically regardless of its shape, shows highly symmetrical feature compared to the background, the area where the symmetry magnitude map achieved through the procedure as described above shows high symmetry depicts the location including the spot or contaminant. Accordingly, the presence of the spot or contaminant is detected and outputted by using the symmetry magnitude map as described above at step 24.

Figure 3:
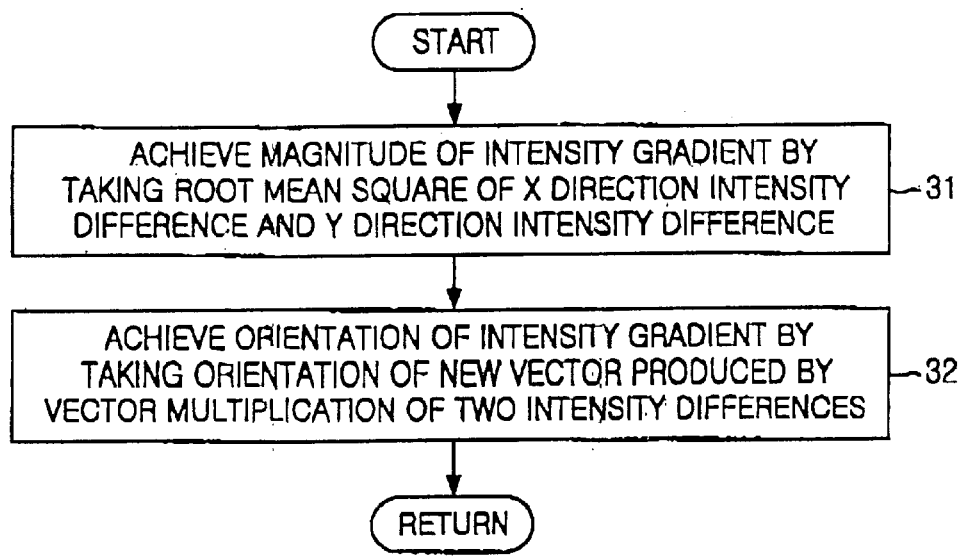
FIG. 3 illustrate a detailed flow chart for an embodiment of a procedure for achieving the magnitude of the intensity gradient and the orientation of the intensity gradient of each pixel in accordance with the present invention.

FIG. 3 is the detailed flow chart of the embodiment of the procedure for achieving the magnitude of the intensity gradient and the orientation of the intensity gradient for each pixel in accordance with the present invention.

First, for each pixel as a reference pixel, the magnitude of the intensity gradient is achieved by producing root mean square of the intensity difference value between the reference pixel and the side adjacent pixel neighboring the reference pixel in x direction (x direction intensity difference value) and the intensity difference value between the reference pixel and the upper or lower adjacent pixel neighboring the reference pixel in y direction (y direction intensity difference value) at step 31.

Then, as representing the two intensity difference values (x direction and y direction intensity difference values) as two vectors in 2 dimensional space, orientation of a new vector produced by multiplying the two vectors is taken as the orientation of the intensity gradient at step 32.

The magnitude and the orientation of the intensity gradient for each pixel achieved by the above procedure is used as basic data measuring the symmetry magnitude around each pixel.

Figure 4:
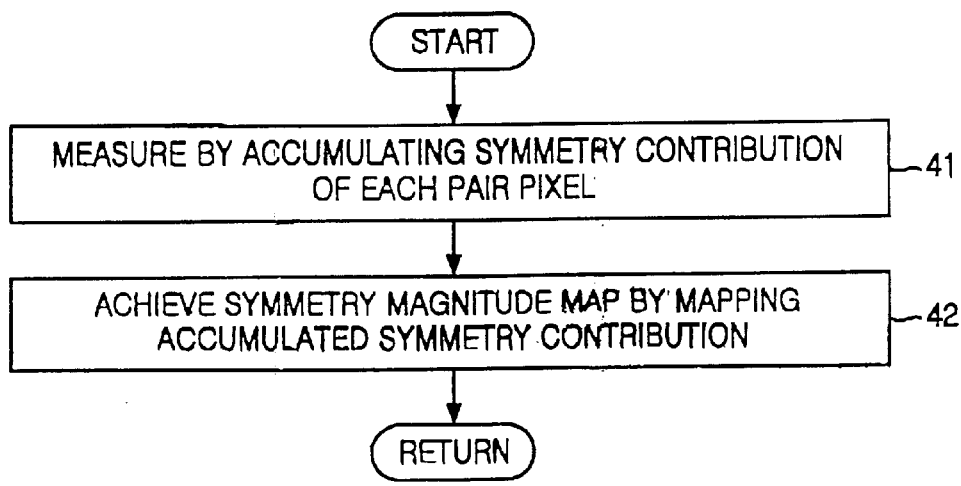
FIG. 4 offers a detailed flow chart for an embodiment of a procedure for achieving a symmetry magnitude map representing symmetry feature of the spot or contaminant in accordance with the present invention.

FIG. 4 is the detailed flow chart of the embodiment for the procedure at step 23 of achieving the symmetry magnitude map of the spot or contaminant in accordance with the present invention.

First, it is accumulated, for each reference pixel, symmetry contribution of symmetry pair pixels located symmetrically to the reference pixel within a certain area of maximum size of the spot or contaminant to measure the symmetry magnitude within the area around each reference pixel at step 41. And then, the symmetry magnitude map is achieved by mapping the symmetry magnitude of each reference pixel in the 2 dimensional space(image coordinates) at step 42.

Thus, the symmetry magnitude map shows the presence of the spot or contaminant by exhibiting the symmetry feature of the spot or contaminant on the surface.

On the other hand, the symmetry contribution for each symmetry pair pixel of the reference pixel is obtained as a product of following 5 terms.

A first term acts as a distance weight function which has smaller value as the distance between the reference pixel and the symmetry pair pixel, i.e., between the symmetry pair, is farther while has larger value as the distance between the reference pixel and the symmetry pair pixel is nearer. Eq. (1) expresses an example of the first term.

$$D_\sigma(i, j) = \frac{1}{\sqrt{2\pi}\sigma} \exp\left(-\frac{\|p_i - p_j\|}{2\sigma^2}\right) \quad (1)$$

where $p_i$ and $p_j$ represent the pixel of the position $(x_i, y_i)$ and $(x_j, y_j)$, respectively, and $\sigma^2$ is the size of the area within which the symmetry contribution is accumulated.

A second term acts as a phase weight function which has larger value as the orientations of the intensity gradient of the two pixels in the symmetry pair are more opposite with each other while has smaller value as the orientations of the intensity gradient of the two pixels in the symmetry pair are more similar to each other. The second term has the maximum value when the orientations are exactly opposite with each other while the second term has 0 value when the orientation are exactly identical to each other. Eq. (2) represents an example of the second term.

$$P(i,j) = \lfloor 1 - \cos(\theta_i + \theta_j - 2a_{ij}) \rfloor \times \lfloor 1 - \cos(\theta_i + \theta_j) \rfloor \quad (2)$$

where $\theta_i$ and $\theta_j$ are the orientations of the pixel $p_i$ and $p_j$, respectively, and $\alpha_{ij}$ is the angle formulated by horizontal line and a line between the pixel $p_i$ and $p_j$.

A third term is a product of the magnitudes of the intensity gradients of the two pixels in the symmetry pair.

A fourth term and a fifth term are terms to eliminate the symmetry contribution due to the background pattern. The fourth and fifth terms use the orientation of the intensity gradient for each pixel.

The fourth term has A value if the orientations of the intensity gradients of the two pixels in the symmetry pair converge to each other while has −A value if the orientation diverge from each other, wherein A is an arbitrary real number.

The fifth term has $\alpha$ value if the orientations of the intensity gradients of the two pixels in the symmetry pair match while has $\beta$ value if the orientations do not match, wherein $\beta > 2\alpha$, $\alpha$ and $\beta$ are arbitrary real numbers.

As the orientations of the intensity gradients of the two pixels in the symmetry pair are more symmetrical to each other, the distance between the two pixels in the symmetry pair is nearer and the magnitudes of the intensity gradients of the two pixels in the symmetry pair are larger, the first, second and third terms have larger values. Since the typical spot or contaminant has high symmetry feature, that is, the spot or contaminant shows high symmetry magnitude at the internal points therein, it is possible to detect the spot or contaminant by achieving such symmetrical points.

However, although it is possible to detect the spot or contaminant by using only these three terms even if the intensity of the background area varies, it is impossible to detect the spot or contaminant when there is pattern in the background area because the symmetry contribution due to the pattern is also accumulated.

Figure 5:
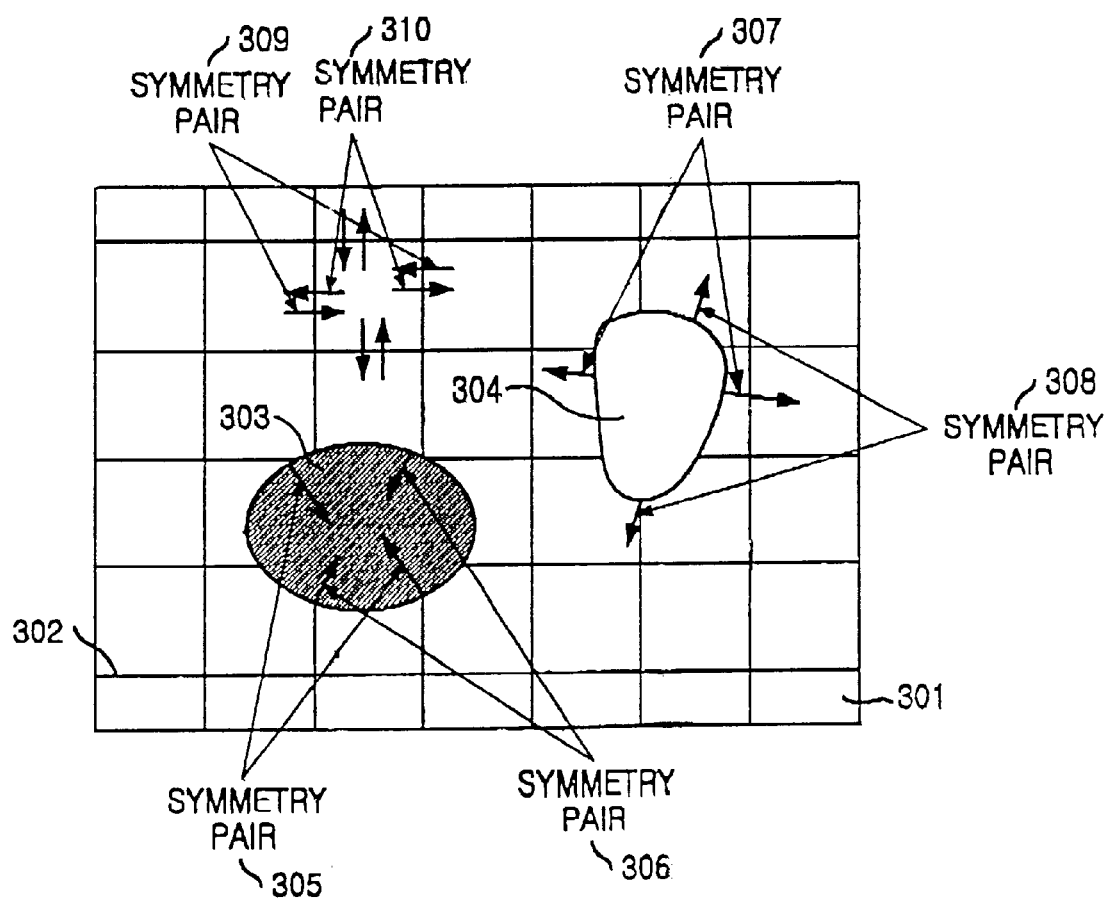
FIG. 5 provides a diagram for explaining the symmetry feature used to detect the spot or contaminant on a surface of an inspected object.

Accordingly, the following fourth and fifth terms should be used. In FIG. 5, the background patterns are aligned pattern-by-pattern in the pattern areas of the background area (i.e., the image formed by 301 and 302). As regarding on selected one of the pattern areas (e.g., the area corresponding to 309 and 310), the orientation of the intensity gradient for each pixel within the pattern diverges 310 outside within the pattern and the orientation of the intensity gradient for each pixel within the adjacent pattern converges 309. Thus, the symmetry contribution due to each pair pixel have signature opposite with each other by fourth term and therefore is not accumulated. Accordingly, the pattern in the background is not detected as the spot or contaminant.

In contrast, within the spot or contaminant area 303 being darker than the background, the orientation of the intensity gradient converges 305, 306 to internal to the spot or contaminant. And within the spot or contaminant area 304 being brighter than the background, the orientation of the intensity gradient diverges 307, 308 to external to the spot or contaminant. Consequently, the symmetry contribution is continuously accumulated within the spot or contaminant area so that the spot or contaminant can be detected.

As described above, the symmetry contribution is produced by multiplying all the 5 terms. Thus, it is possible to detect the spot or contaminant by using that symmetry contribution value regardless of the intensity gradient and the pattern of the background.

Therefore, the present invention has effect to detect the spot or contaminant on the surface when the intensity of the surface of the inspected object is non-uniform or has the pattern in its background.

And the present invention can be applied to more variable objects than the conventional methods, which has capability to performs the surface visual inspection for some assemblies such as a liquid crystal display (LCD) and a back light unit emitting at rear of the LCD.

While the present invention has been described with respect to certain preferred embodiments only, other modifications and variations may be made without departing from the spirit and scope of the present invention as set forth in the following claims.

What is claimed is:

1. An apparatus for inspecting a surface of an object, comprising:

image obtaining means for obtaining an image of the surface of the object; and controlling means for providing a symmetry feature of a spot or contaminant by using a magnitude of an intensity gradient and an orientation of the intensity gradient for each pixel of the obtained surface image to thereby detect the spot or contaminant on the surface, wherein the controlling means obtains the magnitude of the intensity gradient by taking root mean square of the intensity difference value between a reference pixel and a side adjacent pixel neighboring the reference pixel to obtain a first vector and the intensity difference value between the reference pixel and an upper or lower adjacent pixel neighboring the reference pixel to obtain a second vector and then obtains the orientation of the intensity gradient by taking orientation of a new vector produced by multiplying said two vectors representing two intensity difference values in two dimension, respectively.

2. The apparatus of claim 1, wherein the controlling means detects the spot or contaminant by using a symmetry magnitude map formed by the magnitude of the intensity gradient and the orientation of the intensity gradient of each pixel, after obtaining the magnitude of the intensity gradient and the orientation of the intensity gradient by using a gradient operator on the obtained surface image, wherein the symmetry magnitude map provides the internal symmetry feature of the spot or contaminant.

3. The apparatus of claim 2, wherein the controlling means obtains the symmetry magnitude map by accumulating symmetry contribution of each symmetry pair pixel for a reference pixel, each symmetry pair pixel and the reference pixel being included in each symmetry pair for the reference pixel, to measure the symmetry magnitude and mapping the symmetry magnitude for each pixel in image coordinates.

4. The apparatus of claim 3, wherein the symmetry contribution is obtained by multiplying a distance weighting function, phase weighting function, the product of the magnitudes of the intensity gradients of the two pixels in the symmetry pair, a first value representing whether orientations of the intensity gradients of the two pixels in the symmetry pair are converged to each other or diverged from each other, and a second value representing whether orientations of the intensity gradients of the two pixels in the symmetry pair are matched with each other or are different from each other.

5. The apparatus of claim 1, wherein the image obtaining means includes:

power providing means for providing driving power under the control of the controlling means;

moving means driven by the power providing means for moving the object thereon;

input means for inputting the image of the surface of the object placed on the moving means; and image processing means for pre-processing the image from the input means.

6. A method for inspecting a surface of an object, for use in a surface inspecting apparatus, comprising the steps of:

a) obtaining a magnitude of an intensity gradient and an orientation of the intensity gradient of each pixel in an image of the surface by using a gradient operator;

b) obtaining a symmetry magnitude map by using the magnitude of the intensity gradient and the orientation of the intensity gradient of each pixel, wherein the symmetry magnitude map exhibits the internal symmetry feature of a spot or contaminant on the surface; and c) detecting the spot or contaminant by using the symmetry magnitude map, wherein said step a) includes the steps of:

a-1) inputting the image of the surface of the object;

a-2) obtaining the magnitude of the intensity gradient by taking root mean square of the first intensity difference value between a reference pixel and a side adjacent pixel neighboring the reference pixel to obtain a first vector and the second intensity difference value between the reference pixel and an upper or lower adjacent pixel; neighboring the reference pixel to obtain a second vector and a-3) obtaining the orientation of the intensity gradient by taking orientation of a new vector produced by multiplying said two vectors, each representing the first intensity difference value and the second intensity difference value, respectively.

7. The method of claim 6, wherein said step b) includes the steps of:

b-1) measuring the symmetry magnitude in the area around the reference pixel by accumulating symmetry contribution of each symmetry pair pixel located symmetrically to the reference pixel within the area of maximum size of the spot or contaminant, each symmetry pair pixel and the reference pixel being included a symmetry pair; and b-2) obtaining the symmetry magnitude map by mapping the symmetry magnitude of each reference pixel into image coordinates.

8. The method of claim 7, wherein the symmetry contribution is obtained by multiplying a distance weighting function, phase weighting function, the product of the magnitudes of the intensity gradients of the two pixels in the symmetry pair, a first value representing whether orientations of the intensity gradients of the two pixels in the symmetry pair are converged to each other or diverged from each other, and a second value representing whether orientations of the intensity gradients of the two pixels in the symmetry pair are matched with each other or are different from each other.

9. A computer-readable recording medium for storing a program implementing a method for inspecting a surface of an object in an apparatus having a large capability processor the method comprising the steps of:

a) obtaining a magnitude of an intensity gradient and an orientation of an intensity gradient for each pixel of an image of the surface by using a gradient operator on the image;

b) obtaining symmetry magnitude map exhibiting symmetry feature of a spot or contaminant by using the magnitude of the intensity gradient and the orientation of the intensity gradient; and c) detecting the spot or contaminant by using the symmetry magnitude map, wherein said step a) includes the steps of:

a-1) inputting the image of the surface of the object;

a-2) obtaining the magnitude of the intensity gradient by taking root mean square of the first intensity difference value between a reference pixel and a side adjacent pixel neighboring the reference pixel to obtain a first vector and the second intensity difference value between the reference pixel and an upper or lower adjacent pixel; neighboring the reference pixel to obtain a second vector and a-3) obtaining the orientation of the intensity gradient by taking orientation of a new vector produced by multiplying said two vectors, each representing the first intensity difference value and the second intensity difference value, respectively.

* * * * *